(12) United States Patent
Yonehara et al.

(10) Patent No.: US 7,381,539 B2
(45) Date of Patent: Jun. 3, 2008

(54) METHOD OF ASSAY BY OXIDATION-REDUCTION REACTION WITH FORMAZAN

(75) Inventors: Satoshi Yonehara, Kyoto (JP); Kaori Ishimaru, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 60 days.

(21) Appl. No.: 10/515,715

(22) PCT Filed: Apr. 28, 2003

(86) PCT No.: PCT/JP03/05485

§ 371 (c)(1),
(2), (4) Date: Nov. 23, 2004

(87) PCT Pub. No.: WO03/104815

PCT Pub. Date: Dec. 18, 2003

(65) Prior Publication Data

US 2005/0202399 A1  Sep. 15, 2005

(30) Foreign Application Priority Data

Jun. 7, 2002 (JP) ............................. 2002-167764

(51) Int. Cl.
C12Q 1/26 (2006.01)
(52) U.S. Cl. ...................................................... 435/25
(58) Field of Classification Search .................... None
See application file for complete search history.

(56) References Cited

U.S. PATENT DOCUMENTS

| | | |
|---|---|---|
| 4,119,405 A | 10/1978 | Lam |
| 4,310,626 A | 1/1982 | Burkhardt et al. |
| 4,587,220 A | 5/1986 | Mayambala-Mwanika et al. |
| 4,743,559 A | 5/1988 | Koevér et al. |
| 4,755,472 A | 7/1988 | Ismail et al. |
| 4,954,451 A | 9/1990 | Albarella et al. |
| 5,013,647 A | 5/1991 | Town et al. |
| 5,196,314 A | 3/1993 | Town et al. |

FOREIGN PATENT DOCUMENTS

| | | |
|---|---|---|
| EP | 0 990 706 A1 | 4/2000 |
| EP | 1 130 111 A2 | 9/2001 |
| JP | 56-151358 | 11/1981 |
| JP | 57-13357 | 1/1982 |
| JP | 57-161650 | 10/1982 |
| JP | 59-193354 | 11/1984 |
| JP | 61-84 | 6/1986 |
| JP | 62-169053 | 7/1987 |
| JP | 3-30697 | 2/1991 |

OTHER PUBLICATIONS

Yoshida et al. Eur J Biochem 1996;242:499-505.*
Kayamori et al. (Abstract only) Seibutsu Shiryo Bunseki 1996;19(3):168-174.*

* cited by examiner

*Primary Examiner*—Jon P Weber
*Assistant Examiner*—Bin Shen
(74) *Attorney, Agent, or Firm*—Hamre, Schumann, Mueller & Larson, P.C.

(57) ABSTRACT

The present invention provides a highly reliable method of measuring an analyte in a sample using a redox reaction. In this method, a formazan compound is added to a sample prior to a redox reaction so as to eliminate the influence of any reducing substance in the sample. Thereafter, a reducing substance or an oxidizing substance derived from the analyte is formed, and the amount of the formed substance is measured by the redox reaction. The amount of the analyte is determined from the amount of the formed substance thus measured. As the formazan compound, for example, 1-(4-iodophenyl)-3-(2,4-disulfophenyl)-5-(2,4-dinitrophenyl) formazan can be used.

18 Claims, No Drawings

METHOD OF ASSAY BY OXIDATION-REDUCTION REACTION WITH FORMAZAN

This application is a 371 of PCT/JP03/05485 filed Apr. 28, 2003.

TECHNICAL FIELD

The present invention relates to a method of measuring an analyte in a sample using a redox reaction.

BACKGROUND ART

Conventionally, the measurement of the amount of an analyte in a sample using a redox reaction has been utilized for a wide range of applications. For example, such measurement has been utilized for measuring glycated proteins in applications such as biochemical analyses, clinical tests, and the like.

For instance, glycated proteins in blood, particularly glycated hemoglobin (HbA1c) in erythrocytes, are significant indicators in the diagnosis, therapy, and the like of diabetes, because they reflect the patient's past history of blood glucose levels. Glycated proteins in erythrocytes are measured using a redox reaction, for example, in the following manner.

First, erythrocytes are hemolyzed to prepare a sample. This hemolyzed sample is treated with a suitable protease or the like, and then treated with a fructosyl amino acid oxidase (hereinafter referred to as FAOD) so as to form hydrogen peroxide. The amount of the hydrogen peroxide formed corresponds to the amount of a glycated protein in erythrocytes. Then, a peroxidase (hereinafter referred to as POD) and a reducing agent further are added to the reaction solution, so that a redox reaction occurs between the hydrogen peroxide and the reducing agent with the POD as a catalyst. At this time, when a reducing agent that develops color when it is oxidized is used, the amount of the hydrogen peroxide can be determined by measuring the color developed. As a result, the amount of the glycated protein in erythrocytes can be determined.

However, various types of reducing substances, such as ascorbic acid (AsA) and bilirubin, usually are present in blood. Moreover, various types of reducing substances such as glutathione (GSH) are present in erythrocytes. These reducing substances may reduce the hydrogen peroxide, may inhibit the redox reaction, or may reduce the reducing agent after it develops color, so as to degrade the color. Therefore, there has been a problem that it is difficult to determine the amount of the glycated protein in erythrocytes accurately.

Also, there has been another problem that the accuracy of the measurement may deteriorate because the concentrations of the reducing substances contained in samples are not constant.

In order to avoid these problems, for example, various types of oxidizing agents have been added to samples. For example, JP 56(1981)-151358 A discloses a method of using halogen oxides, such as iodic acid or periodic acid, as oxidizing agents. JP 57(1982)-13357 A, JP 57(1982)-161650 A, JP 59(1984)-193354 A, JP 62(1987)-169053 A, and JP 3(1991)-30697 A also disclose methods of using complexes of metals such as cobalt, iron, cerium, etc. as oxidizing agents.

However, the influence of the reducing substances on the measurements cannot be avoided sufficiently even with the use of these oxidizing agents. In particular, these oxidizing agents performed poorly when the analyte is a component in erythrocytes.

DISCLOSURE OF INVENTION

Accordingly, it is an object of the present invention to provide a highly reliable method of measuring an analyte in a sample using a redox reaction.

In order to accomplish this object, the present invention provides a method of measuring an analyte in a sample using a redox reaction, including: eliminating an influence of any reducing substance contained in the sample with a formazan compound. In the present invention, a formazan compound refers to a substituted compound of formazan having a formazan ($H_2NN=CHN=NH$) structure.

The inventors of the present invention already found that the cause of the problems in the conventional methods is not that the influence of the low molecular weight reducing substances such as the above-described GSH and AsA are not eliminated, but that the influence of high molecular weight reducing substances such as proteins are not eliminated. Based on this finding, the inventors of the present invention conducted in-depth researches and finally found that, although formazan compounds are the same type of reducing substances as the low molecular weight reducing substances, they can eliminate the influence of, for example, hemoglobin and degradation products of hemoglobin (hereinafter, both are referred to together as "hemoglobin") unlike the conventional oxidizing agents, thereby having established the method of the present invention. The fact that the influence of the high molecular weight reducing substances as described above can be eliminated by formazan compounds as reducing substances was first discovered by the inventors of the present invention. According to the method of the present invention, the amount of the analyte can be determined with greater reliability. Thus, it is used suitably for various kinds of tests in clinical medicine, for example. The mechanism by which formazan compounds as reducing substances eliminate the influence of reducing substances contained in a sample is considered to be different from that of the conventional oxidizing agents. Moreover, since formazan compounds are very stable, there is no fear that they might affect a redox reaction.

In the method for measurement according to the present invention, it is preferable that the influence of the reducing substance contained in the sample is eliminated by adding the formazan compound to the sample prior to the redox reaction and thereafter, the method preferably further includes: forming a reducing substance or an oxidizing substance derived from the analyte; measuring the amount of the formed substance derived from the analyte by the redox reaction; and determining the amount of the analyte from the amount of the formed substance derived from the analyte.

In the method of the present invention, the formazan compound can be represented, for example, by Formula (1) below. The formazan compound may have substituents ($R^1$, $R^2$, and $R^3$) at least at the 1-position for a nitrogen atom, the 3-position for a carbon atom, and the 5-position for a nitrogen atom of its formazan structure. In Formula (1), $R^1$, $R^2$, and $R^3$ may be hydrogen or substituents described later.

$$R^1N=N-C(R^2)=N-NHR^3 \qquad (1)$$

It is preferable that the formazan compound has substituents with a ring structure (ring substituents) at least at two positions selected from the 1-position for a nitrogen atom, the 3-position for a carbon atom, and the 5-position for a nitrogen atom of its formazan structure. It is more preferable that the formazan compound has ring substituents at three positions.

When the formazan compound has ring substituents at least at two positions as described above, the substituents preferably are at the 1-position for the nitrogen atom and at the 5-position for the nitrogen atom. Furthermore, when the formazan compound has ring substituents at three positions as described above, the substituents preferably are at the 1-position for the nitrogen atom, the 3-position for the carbon atom, and the 5-position for the nitrogen atom.

Furthermore, it is preferable that at least two ring substituents of the formazan compound have a benzene ring structure. Besides the benzene ring structure, the ring substituents may have a resonance structure with S or O being contained in the ring structure, for example. Examples of the ring substituents with such a resonance structure include a thienyl group, thiazoyl group, and the like.

Still further, it is preferable that the formazan compound has ring substituents at least at the 1-position for a nitrogen atom, the 3-position for a carbon atom, and the 5-position for a nitrogen atom of its formazan structure, and that at least two of the ring substituents have a benzene ring structure.

Still further, it is preferable that at least one of the ring substituents has a functional group, and a larger number of functional groups are more preferable.

Preferable examples of the functional group include electron-withdrawing functional groups such as a halogen group, ether group, ester group, carboxy group, acyl group, nitroso group, nitro group, hydroxy group, and sulfo group. Examples other than these functional groups include characteristic groups containing oxygen such as a hydroperoxy group, oxy group, epoxy group, epidioxy group, and oxo group; and characteristic groups containing sulfur such as a mercapto group, alkylthio group, methylthiomethyl group, thioxo group, sulfino group, benzenesulfonyl group, phenylsulfonyl group, p-toluenesulfonyl group, p-tolylsulfonyl group, tosyl group, sulfamoyl group, and isothiocyanate group. Among these electron-withdrawing functional groups, a nitro group, sulfo group, halogen group, carboxy group, hydroxy group, methoxy group, ethoxy group are preferable. Examples other than the above-described electron-withdrawing functional groups include unsaturated hydrocarbon groups such as a phenyl group ($C_6H_5-$) and styryl group ($C_6H_5CH=CH-$). It is to be noted that the functional groups may have been ionized by dissociation.

Still further, it is preferable that the formazan compound has benzene rings (phenyl groups) at the 1-position for a nitrogen atom and at the 5-position for a nitrogen atom of its formazan structure, and that at least one of the benzene rings (phenyl groups) has at least one functional group selected from the group consisting of a halogen group, carboxy group, nitro group, hydroxy group, sulfo group, methoxy group, and ethoxy group. It is to be noted here that both the benzene rings (phenyl groups) may have such a functional group. Moreover, the functional group may be at any positions (ortho-, meta-, pra-) on each of the benzene rings (phenyl groups). Furthermore, the number of the functional groups is not specifically limited, and the benzene ring may have either the same or different functional groups.

Examples of the formazan compound having ring substituents with a benzene ring structure at the 1-position for a nitrogen atom, the 3-position for a carbon atom, and the 5-position for a nitrogen atom of its formazan structure include:

1-(4-iodophenyl)-3-(2,4-disulfophenyl)-5-(4-nitrophenyl)-formazan;
1-(4-iodophenyl)-3-(2,4-disulfophenyl)-5-(2,4-dinitrophenyl) formazan;
1-(2-methoxy-4-nitrophenyl)-3-(2,4-disulfophenyl)-5-(4-nitrophenyl)-formazan;
1-(4-iodophenyl)-3-phenyl-5-(4-nitrophenyl)-formazan;
3-(4-chlorophenyl)-1,5-(diphenyl) formazan;
1,3-diphenyl-5-(p-diphenyl) formazan;
3-(p-diphenyl)-1,5-(diphenyl) formazan;
1,3-diphenyl-5-(4-styrylphenyl) formazan;
1,3-diphenyl-5-(m-tolyl) formazan; and
1,3-diphenyl-5-(p-tolyl) formazan.

The formazan compound is not limited to those described above. In addition to the above-described formazan compounds, formazan compounds having ring substituents with a benzene ring structure at two positions selected from the 1-position for a nitrogen atom, the 3-position for a carbon atom, and the 5-position for a nitrogen atom of its formazan structure and a ring substituent having a structure other than the benzene ring structure at one position excluding the above-described two positions also may be used. Examples of such formazan compounds include:
3-(2-thienyl)-1,5-(diphenyl) formazan;
1-benzothiazoyl-3-[4-(2-sulfoethyl carbamoyl) phenyl]-5-(4-carboxy-2-methoxyphenyl) formazan; and
1,3-diphenyl-3-(4,5-dimethyl-2-thiazoyl) formazan.

Furthermore, formazan compounds having ring substituents with a benzene ring structure at two positions selected from the 1-position for a nitrogen atom, the 3-position for a carbon atom, and the 5-position for a nitrogen atom of its formazan structure and a ring substituent not having a ring structure at one position excluding the above-described two positions also may be used. Examples of such a formazan compound include:
3-cyano-1,5-(diphenyl) formazan;
3-carboxy-1,5-(diphenyl) formazan;
3-methyl-1,5-(diphenyl) formazan; and
3-ethyl-1,5-(diphenyl) formazan.

Besides the above-described formazan compounds, 5,5'-[3,3'-dimethoxy-(1,1'-biphenyl) 4,4'-diyl]-bis[1-(4-nitrophenyl)-3-phenylformazan], 1-(4,5-dimethylthiazole-2-yl)-3,5-diphenylformazan, and the like also may be used, for example.

Among the above-described formazan compounds, preferable are those having three ring substituents as described above, and more preferable are those having three ring substituents with a benzene ring structure and having many electron-withdrawing functional groups. Particularly preferable is 1-(4-iodophenyl)-3-(2,4-disulfophenyl)-5-(2,4-dinitrophenyl) formazan. It is to be noted here that such formazan compounds may be salts or may have been ionized, for example.

In the method of the present invention, the amount of the formazan compound added is not particularly limited, and it can be determined as appropriate depending on the type of the sample and the amount of the reducing substance contained in the sample. Specifically, it is preferable that the formazan compound is added so that its concentration falls in the range from 0.001 to 100 μmol, more preferably from 0.005 to 10 μmol, and particularly preferably from 0.01 to 1 μmol per 1 μl of the sample.

In the method of the present invention, when the sample is whole blood, it is preferable that the formazan compound is added so that its concentration falls in the range from 0.001 to 10 μmol, more preferably from 0.005 to 5 μmol, and particularly preferably from 0.01 to 1 μmol per 1 μl of whole blood. Specifically, when the formazan compound is 1-(4-iodophenyl)-3-(2,4-disulfophenyl)-5-(2,4-dinitrophenyl) formazan, it preferably is added so that its concentration falls in the range from 0.001 to 0.4 µmol, more preferably from 0.005 to 0.1 µmol, and particularly preferably from 0.01 to 0.07 µmol per 1 µl of whole blood.

For example, in the method of the present invention, the redox reaction preferably is a color-developing reaction caused by reducing the oxidizing substance derived from the analyte and oxidizing a substrate that develops color by oxidation (color-developing substrate) using an oxidase. The amount of the oxidizing substance preferably is measured by measuring the degree of the color developed in the color-developing reaction. Preferably, the degree of the color developed is measured by measuring the absorbance at the wavelength for detecting the substrate.

When the color-developing reaction is caused between the oxidizing substance derived from the analyte and the color-developing substrate using the oxidase and the degree of the color developed by the color-developing substrate by oxidization is measured by measuring the absorbance as described above, it is preferable that the wavelength for detecting the color-developing substrate is different from the absorption wavelength of the formazan compound.

Although not particularly limited, it is preferable that, for example, N-(carboxymethylaminocarbonyl)-4,4'-bis(dimethylamino)diphenylamine sodium salt (e.g., a product named DA-64, manufacture by Wako Pure Chemical Industries, Ltd.) is used as the color-developing substrate, because this can be detected with high sensitivity. Furthermore, it is preferable that the oxidase is a peroxidase (POD).

In the method of the present invention, it is preferable that the oxidizing substance derived from the analyte is hydrogen peroxide, and that the amount of the analyte is determined by measuring the amount of the hydrogen peroxide. The amount of the hydrogen peroxide can be determined by, for example, causing the hydrogen peroxide to be reduced and the color-developing substrate to be oxidized by the action of a POD as the oxidase and then measuring the degree of the color developed by the substrate.

In the method of the present invention, the type of the sample is not particularly limited. The method also can be applied to samples other than whole blood, plasma, serum, and blood cells, e.g. biological samples such as urine and spinal fluid, drinks such as juices, and foods such as soy sauce and Worcestershire sauce.

In the method of the present invention, the analyte may be, for example, components in whole blood, components in erythrocytes, components in plasma, components in serum, components in urine, components in spinal fluid, and the like, and it preferably is a component in erythrocytes. The component in erythrocytes may be, for example, glycated proteins such as glycated hemoglobin and glycated albumin, glycated peptides, glycated amino acids, glucose, uric acid, cholesterol, creatinine, sarcosine, glycerol, and the like. Among these, glycated proteins are more preferable. For example, when a component in erythrocytes is to be measured, whole blood itself may be hemolyzed to prepare a sample, or erythrocytes are separated from whole blood and hemolyzed to prepare a sample.

In the method of the present invention, when the analyte is a glycated protein, it is preferable that a FAOD is caused to act on the analyte so that hydrogen peroxide is formed as the oxidizing substance derived from the analyte. Also, when the analyte is a glycated amine such as a glycated peptide or a glycated amino acid, it is preferable that the analyte similarly is subjected to the action of a FAOD.

Moreover, it is preferable that glycated proteins and glycated peptides are treated with a protease before its treatment with a FAOD as necessary.

As the FAOD, a FAOD catalyzing a reaction represented by Formula (2) below preferably is used.

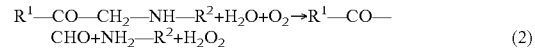
$$R^1—CO—CH_2—NH—R^2 + H_2O + O_2 \rightarrow R^1—CO—CHO + NH_2—R^2 + H_2O_2 \quad (2)$$

In Formula (2), $R^1$ denotes a hydroxyl group or a residue derived from the sugar before glycation (i.e., sugar residue). The sugar residue ($R^1$) is an aldose residue when the sugar before glycation is aldose, and is a ketose residue when the sugar before glycation is ketose. For example, when the sugar before glycation is glucose, it takes a fructose structure after glycation by an Amadori rearrangement. In this case, the sugar residue ($R^1$) becomes a glucose residue (an aldose residue). This sugar residue ($R^1$) can be represented, for example, by

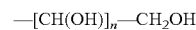
$$—[CH(OH)]_n—CH_2OH$$

where n is an integer of 0 to 6.

In Formula (2), $R^2$ is not particularly limited. However, when the substrate is a glycated amino acid, a glycated peptide, or a glycated protein, for example, there is a difference between the case where an α-amino group is glycated and the case where an amino group other than the α-amino group is glycated.

In Formula (2), when an α-amino group is glycated, $R^2$ is an amino acid residue or a peptide residue represented by Formula (3) below.

$$—CHR^3—CO—R^4 \quad (3)$$

In Formula (3), $R^3$ denotes an amino-acid side chain group. $R^4$ denotes a hydroxyl group, an amino acid residue, or a peptide residue, and can be represented, for example, by Formula (4) below. In Formula (4), n is an integer of 0 or more, and $R^3$ denotes an amino-acid side chain group as in the above.

$$—(NH—CHR^3—CO)_n—OH \quad (4)$$

In Formula (2), when an amino group other than the α-amino group is glycated (i.e., an amino-acid side chain group is glycated), $R^2$ can be represented by Formula (5) below.

$$—R^5—CH(NH—R^6)—CO—R^7 \quad (5)$$

In Formula (5), $R^5$ denotes a portion other than the glycated amino group in the amino-acid side chain group. For example, when the glycated amino acid is lysine, $R^5$ is as follows.

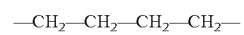
$$—CH_2—CH_2—CH_2—CH_2—$$

For another example, when the glycated amino acid is arginine, $R^5$ is as follows.

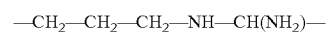
$$—CH_2—CH_2—CH_2—NH—CH(NH_2)—$$

In Formula (5), $R^6$ denotes hydrogen, an amino acid residue, or a peptide residue, and can be represented, for example, by Formula (6) below.

In Formula (6), n denotes an integer of 0 or more, and $R^3$ denotes an amino-acid side chain group as in the above.

$$—(CO—CHR^3—NH)_n—H \quad (6)$$

In Formula (5), $R^7$ denotes a hydroxyl group, an amino acid residue, or a peptide residue, and can be represented, for example, by Formula (7) below. In Formula (7), n is an integer of 0 or more, and $R^3$ denotes an amino-acid side chain group as in the above.

$$—(NH—CHR^3—CO)_n—OH \quad (7)$$

Furthermore, it is preferable that the reducing substance contained in the sample is a protein. The molecular weight of the protein is, for example, at least 3,000, preferably from 3,000 to 3,000,000, more preferably from 10,000 to 300,000, and particularly preferably from 30,000 to 100,000. Examples of such a reducing substance include hemoglobin, globin, globulin, and albumin. Among these, hemoglobin is preferable.

BEST MODE FOR CARRYING OUT THE INVENTION

Hereinafter, the method of the present invention will be described in detail with reference to the following examples, in which a glycated protein in blood cells is measured.

First, whole blood itself is hemolyzed, or a blood cell fraction is separated from whole blood in the usual way such as centrifugation and then hemolyzed, so as to prepare a hemolyzed sample. The method of causing the hemolysis is not particularly limited, and can be, for example, a method using a surfactant, a method using ultrasonic waves, and a method utilizing a difference in osmotic pressure. Among these, the method using a surfactant is preferable because of its simplicity in operation, etc.

As the surfactant, for example, non-ionic surfactants such as polyoxyethylene-p-t-octylphenyl ether (e.g. Triton series surfactants), polyoxyethylene sorbitan alkyl ester (e.g. Tween series surfactants), polyoxyethylene alkyl ether (e.g. Brij series surfactants), and the like can be used. Specific examples are Triton X-100, Tween-20, Brij 35, and the like. The conditions of the treatment with the surfactant usually are as follows: when the concentration of blood cells in the solution to be treated is in the range from 1 to 10 vol %, the surfactant is added so that its concentration in the solution falls in the range from 0.01 to 5 wt %, and stirred at room temperature for about several seconds (about 5 seconds) to 10 minutes.

Next, the formazan compound is added to the hemolyzed sample to carry out pretreatment of the sample.

For example, when the concentration of blood cells in the solution to be pretreated is in the range from 1 to 10 vol %, it is preferable that the formazan compound is added so that its concentration falls in the range from 0.02 to 2000 mmol/l, more preferably from 0.1 to 1000 mmol/l, and particularly preferably from 0.4 to 200 mmol/l. Specifically, when the formazan compound is 1-(4-iodophenyl)-3-(2,4-disulfophenyl)-5-(2,4-dinitrophenyl)-formazan, preferably it is added so that its concentration falls in the range from 0.02 to 80 mmol/l, more preferably from 0.1 to 20 mmol/l, and particularly preferably from 0.2 to 15 mmol/l.

The pretreatment usually is carried out in a buffer. For example, CHES buffer, CAPSO buffer, CAPS buffer, phosphate buffer, Tris buffer, EPPS buffer, HEPES buffer, and the like can be used. The pH of the buffer is, for example, in the range from 6 to 13, preferably from 8 to 12, and more preferably from 9 to 11. Moreover, the final concentration of the buffer in the solution is, for example, from 1 to 400 mmol/l, preferably from 10 to 200 mmol/l.

The conditions of the pretreatment are not particularly limited, but it usually is carried out at a temperature of 10° C. to 37° C. for a period of 10 seconds to 60 minutes.

Although the formazan compound may be used simply as it is, it preferably is used as a solution in which the formazan compound is dissolved in a solvent, in terms of simplicity of operation, efficiency of the treatment, etc. The concentration of the solution can be determined as appropriate depending on the type of the formazan compound (e.g. molecular weight or the like), etc. For example, the concentration is in the range from 0.01 to 120 mmol/l, preferably from 0.1 to 50 mmol/l, and more preferably from 0.2 to 20 mmol/l. As the solvent, for example, distilled water, physiological saline, buffers, and the like can be used. As the buffers, for example, the same buffers as described above can be used. Moreover, the formazan compound may be used either alone or in combinations of two or more types.

Next, the pretreated hemolyzed sample is treated with a protease. This treatment is performed so that the FAOD used in the subsequent treatment may act on the analyte more easily.

The type of the protease is not particularly limited, and for example, proteinase K, subtilisin, trypsin, aminopeptidase, and the like can be used. The protease treatment usually is carried out in a buffer, and the conditions of the treatment are determined as appropriate depending on the type of the protease used, the type and the concentration of the glycated protein as the analyte, etc.

Specifically, when the pretreated hemolyzed sample is treated using proteinase K as the protease, the protease treatment usually is carried out, for example, under the conditions as follows: the concentration of the protease in the reaction solution in the range from 10 to 30,000 mg/l; the concentration of blood cells in the reaction solution in the range from 0.05 to 15 vol %; a reaction temperature in the range from 15° C. to 37° C.; a reaction period in the range from 1 minute to 24 hours; and a pH in the range from 6 to 12. Moreover, the type of the buffer is not particularly limited, and for example, Tris-HCl buffer, EPPS buffer, PIPES buffer, and the like can be used.

Next, a degradation product obtained by the protease treatment further is treated with the FAOD. The reaction shown by Formula (2) above is catalyzed by this FAOD treatment.

It is preferable that the FAOD treatment is carried out in a buffer as in the above protease treatment. The conditions of the FAOD treatment are determined as appropriate depending on the type of the FAOD used, the type and the concentration of the glycated protein as the analyte, etc.

Specifically, the conditions are as follows: the concentration of the FAOD in the reaction solution in the range from 50 to 50,000 U/l; the concentration of blood cells in the reaction solution in the range from 0.01 to 1 vol %; a reaction temperature in the range from 15° C. to 37° C.; a reaction period in the range from 1 to 60 minutes; and a pH in the range from 6 to 9. Moreover, the type of the buffer is not particularly limited, and for example, the same buffers as in the protease treatment can be used.

Next, the hydrogen peroxide formed in the FAOD treatment is measured by a redox reaction using a POD and the color-developing substrate.

Examples of the color-developing substrate include N-(carboxymethylaminocarbonyl)-4,4'-bis(dimethylamino) diphenylamine sodium salt (hereinafter also referred to as "DA-64"), orthophenylenediamine (OPD) and a substrate in which trinder's reagent and 4-aminoantipyrine (4AA) are combined. Examples of the trinder's reagent are phenol, phenol derivatives, aniline derivatives, naphthol, naphthol derivatives, naphthylamine, and naphthylamine derivatives. Specifically, N-Ethyl-N-(2-hydroxy-3-sulfopropyl)-3-methylaniline, sodium salt, dihydrate (TOOS); N-Ethyl-N-(2-hydroxy-3-sulfopropyl)-3,5-dimethylaniline, sodium salt, monohydrate (MAOS); N-Ethyl-N-(2-hydroxy-3-sulfopropyl)-3,5-dimethoxyaniline, sodium salt (DAOS); and the like can be used. Moreover, in place of the aminoantipyrine, aminoantipyrine derivatives, vanillin diamine sulfonic acid, methylbenzothiazolinone hydrazone (MBTH), sulfonated methylbenzothiazolinone hydrazone (SMBTH), and the like, also can be used. Among these color-developing substrates, particularly preferable is N-(carboxymethylaminocarbonyl)-4,4'-bis(dimethylamino)diphenylamine sodium salt (DA-64), as described above.

The redox reaction usually is carried out in a buffer. The conditions of the reaction are determined as appropriate depending on the concentration of the hydrogen peroxide formed, etc. The conditions are usually as follows: the concentration of the POD in the reaction solution in the range from 10 to 100,000 IU/l; the concentration of the color-developing substrate in the range from 0.005 to 30 mmol/l; a reaction temperature in the range from 15° C. to 37° C.; a reaction period in the range from 0.1 to 30 minutes; and a pH in the range from 5 to 9. Moreover, the type of the buffer is not particularly limited, and for example, the same buffers as in the protease treatment and the FAOD treatment can be used.

In the redox reaction, for example, when the color-developing substrate is used, the amount of the hydrogen peroxide can be determined by measuring the degree of the color developed (i.e. absorbance) in the reaction solution with a spectrophotometer. Then, the amount of the glycated protein in the sample can be determined using the concentration of the hydrogen peroxide and a calibration curve or the like, for example.

It is known that many of formazan compounds are dye compounds and they exhibit absorption at wavelengths specific thereto. When the degree of the color developed is measured by measuring an absorbance as describe above, by using a formazan compound that exhibits absorption at a wavelength different from the absorption wavelength of the color developed by the color-developing substrate used, the measurement error due to the formazan compound can be prevented.

Specific examples of formazan compounds and the values of λmax thereof and specific examples of color-developing substrates and the values of λmax thereof are shown below. Based on the values of λmax of the respective formazan compounds and color-developing substrates, the following combinations of the color-developing substrate and the formazan compound are considered as preferable: the combination of the color-developing substrate (1) with the formazan compound (2), (3), or (5); the combination of the color-developing substrate (2) with any one of the formazan compounds (1) to (5); the combination of the color-developing substrate (3) with any one of the formazan compounds (1) to (5); and the combination of the color-developing substrate (4) with the formazan compound (2), (3), or (5). It is to be noted that the combinations listed above are for illustration only, and the combination of the color-developing substrate and the formazan compound is not particularly limited.

(Formazan Compounds and λmax)
(1) 5,5'-[3,3'-dimethoxy-(1,1'-biphenyl) 4,4'-diyl]-bis[1-(4-nitrophenyl)-3-phenylformazan]λmax=530 (nm)
(2) 1-(4-iodophenyl)-3-(2,4-disulfophenyl)-5-(4-nitrophenyl)-formazan λmax=438 (nm)
(3) 1-(4-iodophenyl)-3-phenyl-5-(4-nitrophenyl)-formazan λmax=490 (nm)
(4) 1-(4,5-dimethylthiazole-2-yl)-3,5-diphenylformazan λmax=565 (nm)
(5) 1-(4-iodophenyl)-3-(2,4-disulfophenyl)-5-(2,4-dinitrophenyl) formazan λmax=433 (nm)

(Color-developing Substrates and λmax)
(1) combination of TOOS and 4AA λmax=555 (nm)
(2) combination of MAOS and 4AA λmax=630 (nm)
(3) DA-64 λmax=723 (nm)
(4) combination of DAOS and 4AA λmax=593 (nm)

The amount of the hydrogen peroxide can be determined not only by the above-described enzymatic method using a POD or the like but also by an electrical method, for example.

In this method for measurement, the pretreatment step with a formazan compound is not particularly limited as long as it is carried out before the redox reaction actually occurs as described above. However, because the hydrogen peroxide is formed after the FAOD treatment, it is preferable that the pretreatment step is performed before the FAOD treatment. Moreover, although each of the treating steps may be carried out separately as described above, some of the treating steps also may be performed simultaneously, for example, in the combinations as follows:

1: hemolysis treatment+pretreatment
   2: hemolysis treatment+pretreatment+protease treatment
   3: protease treatment+FAOD treatment
   4: FAOD treatment+POD redox treatment
   5: protease treatment+FAOD treatment+POD redox treatment Furthermore, the order of adding the FAOD, the POD, and the color-developing substrate also is not particularly limited.

Thus, by contacting a sample with a formazan compound, not only the influence of low molecular weight reducing substances such as GSH, AsA, dithiothreitol, cysteine, and N-acetyl-cysteine, but also the influence of, for example, proteins or reducing substances having molecular weights in the above-described range can be avoided.

Furthermore, in the pretreatment step with the formazan compound in the method of the present invention, for example, various oxidizing agents other than the formazan compound as a reducing substance further may be used in combination. Examples of the oxidizing agents include halogen oxides such as sodium iodoacetate, iodic acid, and periodic acid, EDTA-Fe, ascorbic acid oxidase, and bilirubin oxidase. The amount of such an oxidizing agent to be added is, for example, in the range from 0.001 to 0.1 mg per 1 μl of the sample.

In the method of the present invention, the analyte is not particularly limited, as long as a redox reaction is utilized. Examples of the analyte other than the glycated protein include glycated peptides, glycated amino acids, glucose, cholesterol, uric acid, creatinine, sarcosine, and glycerol, as described above.

When the amount of each of the above-described examples of the analyte is measured by forming hydrogen peroxide, the hydrogen peroxide is formed, for example, by action of a glucose oxidase on the glucose; a cholesterol oxidase on the cholesterol; a uricase on the uric acid; a sarcosine oxidase on the creatinine; a sarcosine oxidase on the sarcosine; or a glycerol oxidase on the glycerol; respectively. The amount of the hydrogen peroxide can be measured in the same manner as described above. Moreover, glycated peptides and glycated amino acids can be measured, for example, in the same manner as in the measurement of the glycated protein described above.

Furthermore, after the treatment of the reducing substances in a sample with the formazan compound, when the amount of the analyte is determined by forming a reducing substance derived from the analyte, measuring the amount of the reducing substance by a redox reaction, and determining the amount of the analyte from the amount of the reducing substance thus measured, the measurement can be carried out, for example, in the following manner.

When the analyte is glucose, for example, a reducing substance such as NADH or NADPH is formed using glucose dehydrogenase in the presence of NAD, NADP, or the like. Then, the NADH or NADPH as a reducing substance derived from the analyte is measured by a redox reaction, using, for example, diaphorase and a substrate that develops color by reduction. Then, as described above, the amount of the analyte in the sample can be determined, for example, using the concentration of the reducing substance derived from the analyte and a calibration curve or the like. Furthermore, for example, cholesterol dehydrogenase can be used when the analyte is cholesterol, and sarcosine dehydrogenase can be used when the analyte is sarcosine.

As the substrate that develops color by reduction, although not particularly limited, for example, 2,6-dichlorophenolindophenol or the like may be used. Moreover, in order to obtain measured values with more excellent reliability, for example, it is preferable to measure an absorbance in advance before measuring the reducing substance derived from the analyte.

Moreover, when a sample is thus treated with the formazan compound, the influence of the above-described high molecular weight reducing substances such as proteins can be avoided. Therefore, when there is an influence of a reducing substance having a molecular weight of at least 10,000 or a reducing substance as a protein, the method can be applied not only to the whole blood sample, but also to the above-described various types of samples. Moreover, when a sample other than the whole blood sample is used, the measurement can be carried out in the same manner using the same reagents, except that the sample is different.

EXAMPLES

Hereinafter, the present invention will be described with reference to the following example and comparative example.

Example 1, Comparative Example 1

In Example 1, a sample was pretreated with a formazan compound so as to eliminate the influence of reducing substances in the sample. The reagents and procedure used in Example 1 are shown below.

(Hb Sample)

As a Hb sample, lyophilized purified Hb with a HbA1c concentration of 6.7% was used.

(Formazan Compound)

As the formazan compound, 1-(4-iodophenyl)-3-(2,4-disulfophenyl)-5-(2,4-dinitrophenyl) formazan (product name WSF 3, manufactured by Dojindo Laboratories) represented by the following formula was used.

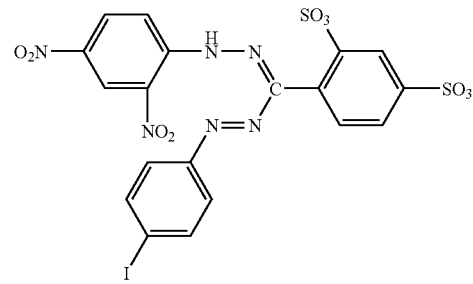

(Fructosyl Valine Solution)

Fructosyl valine (hereinafter referred to as FV) was produced in accordance with the method disclosed in JP 2(1990)-69644 A. The FV was dissolved in purified water so as to prepare a 10 mM FV solution.

(Hemolysis Reagent)

A hemolysis reagent was prepared by adding a surfactant (product name Nikkol, manufactured by Nikko Chemicals Co. Ltd.) to buffer (pH 9.4) containing 40 mM CHES and 15 mM MOPS so that the concentration of the surfactant became 7.5%.

(Pretreatment Reagents)

| WSF 3 | 0 mM; | 0.25 mM; | 1.7 mM |
|---|---|---|---|
| NaN$_3$ | | | 0.043 g/l |
| CaCl$_2$ | | | 2.5 mM |
| NaCl | | | 50 mM |
| MES—MES•Na (pH 5.5) | | | 1 mM |

(Color-Developing Reagent)

| FAOD | 17.5 KU/l |
|---|---|
| POD | 67 KU/l |
| Product named DA-64 | 70 µM |
| (Wako Pure Chemical Industries, Ltd.) | |
| Tris-HCl (pH 7.0) | 300 mM |

(Procedure)

First, 0.123 ml of the 10 mM FV solution and 1.877 ml of the hemolysis reagent were added to 10 mg of the Hb sample to prepare a test sample. Then, 75.6 µl of the pretreatment reagents with the predetermined concentrations of the WSF 3 respectively were added to 8.4 µl of this test sample, and the resultant mixtures were treated at 37° C. for 5 minutes. Thereafter, 18.9 µl of the color-developing reagent further was added to the respective mixtures and the color-developing reaction was allowed to occur at 37° C. for 3 minutes (the total amount of each mixture: 102.9 ul). Then, with regard to the reaction solutions obtained after the color-developing reaction, the absorbance at the wavelength of 726 nm was measured. It is to be noted that the WSF 3 does not affect the detection of the DA-64 because the absorption wavelength of the WSF 3 is around 430 nm.

On the other hand, as a control, measurement was carried out in the same manner as in the above except that a test sample prepared by merely mixing 0.123 ml of the 10 mM FV solution and 1.877 ml of the hemolysis reagent without adding 10 mg of the Hb sample was used. Furthermore, as Comparative Example 1, the same measurement as in Example 1 was carried out except that a pretreatment reagent prepared without adding the WSF 3 was used.

Then, the measured values were substituted into the following equation, and a relative value (%) was determined by setting the absorbance of the control as 100 %. Table 1 below shows the result of the measurement carried out using the pretreatment reagent containing 1.7 mM of the WSF 3.

Relative value (%)=$[(X_1-X_0/Y_1-Y_0)]\times 100$ $X_1$: absorbance after 8 min. from the start of the color-developing reaction $X_0$: absorbance at the start of the color-developing reaction $Y_1$: absorbance after 8 min. from the start of the color-developing reaction in control $Y_0$: absorbance at the start of the color-developing reaction in control

TABLE 1

| | WSF 3 concentration (mM) | Relative value (%) |
|---|---|---|
| Example | 1.7 | 32 |
| Comparative Example | 0 | 1 |
| Control | 1.7 | 100 |

Thus, when the test sample containing Hb as a reducing substance that affects measurement using a redox reaction was treated with the formazan compound, the influence of the reducing substance in the sample was eliminated, so that the reliability of the measurement was improved.

INDUSTRIAL APPLICABILITY

As specifically described above, according to the method of measuring an analyte in a sample according to the present invention, the influence of reducing substances in the sample can be eliminated by adding a formazan compound to the sample. As a result, highly reliable measurement of the analyte becomes possible. Therefore, the method of the present invention is applicable to various analyses in the field of clinical medicine, for example, and particularly is useful for measurement of glycated proteins such as glycated hemoglobin in erythrocytes, which are important in the diagnosis of diabetes.

The invention claimed is:

1. A method of measuring an analyte in a sample comprising a reducing protein using a redox reaction, comprising:
   mixing a formazan compound with the sample comprising the analyte and the reducing protein;
   forming an oxidizing substance derived from the analyte;
   conducting a redox reaction using an oxidase where the analyte derived oxidizing substance is reduced and a substrate that develops color by oxidation is oxidized; and
   measuring the analyte by measuring degree of the color developed in the redox reaction.

2. The method according to claim 1, wherein the formazan compound has substituents with a ring structure at least at two positions selected from the 1-position for a nitrogen atom, the 3-position for a carbon atom, and the 5-position for a nitrogen atom of its formazan structure.

3. The method according to claim 2, wherein the formazan compound has the substituents at least at the 1-position for the nitrogen atom and at the 5-position for the nitrogen atom of its formazan structure.

4. The method according to claim 3, wherein the formazan compound has benzene rings (phenyl groups) as the substituents at the 1-position for the nitrogen atom and the 5-position for the nitrogen atom of its formazan structure.

5. The method according to claim 4, wherein the formazan compound has the benzene rings (phenyl groups) as the substituent at the 1-position for the nitrogen atom and at the 5-position for the nitrogen atom of its formazan structure, and at least one of the benzene rings (phenyl groups) has at least one functional group selected from the group consisting of a halogen group, carboxy group, nitro group, hydroxy group, sulfo group, methoxy group, and ethoxy group.

6. The method according to claim 1, wherein the formazan compound is 1-(4-iodophenyl)-3-(2,4-disulfophenyl)-5-(2,4-dinitrophenyl) formazan.

7. The method according to claim 1, wherein the degree of the color developed is measured by measuring an absorbance at a wavelength for detecting the substrate.

8. The method according to claim 7, wherein the wavelength for detecting the substrate is different from an absorption wavelength of the formazan compound.

9. The method according to claim 1, wherein the oxidizing substance derived from the analyte is hydrogen peroxide.

10. The method according to claim 1, wherein the oxidase is a peroxidase.

11. The method according to claim 1, wherein the analyte is at least one selected from the group consisting of glycated proteins, glycated peptides, and glycated amino acids, and hydrogen peroxide is formed as the oxidizing substance derived from the analyte by treating the analyte with a fructosyl amino acid oxidase.

12. The method according to claim 11, wherein the formazan compound is added to the sample before treating the analyte with the fructosyl amino acid oxidase.

13. The method according to claim 11, wherein a protease treated analyte is then subjected to fructosyl amino acid oxidase treatment.

14. The method according to claim 1, wherein the analyte is at least one selected from the group consisting of glycated proteins, glycated peptides, and glycated amino acids.

15. The method according to claim 14, wherein the glycated protein is glycated hemoglobin.

16. The method according to claim 15, wherein the formazan compound is added to the sample so that its concentration falls in a range from 0.02 to 2000 mmol/l when a concentration of blood cells in the sample is in a range from 1 to 10 vol %.

17. The method according to claim 1, wherein the sample is a hemolyzed sample obtained by hemolyzing erythrocytes.

18. The method according to claim 1, wherein the formazan compound and the sample are mixed by mixing a solution of formazan compound with the sample.

* * * * *